(12) United States Patent
Du et al.

(10) Patent No.: US 7,734,076 B2
(45) Date of Patent: *Jun. 8, 2010

(54) MATERIAL DECOMPOSITION IMAGE NOISE REDUCTION

(75) Inventors: Yanfeng Du, Rexford, NY (US); John Eric Tkaczyk, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 848 days.

This patent is subject to a terminal disclaimer.

(21) Appl. No.: 11/609,262

(22) Filed: Dec. 11, 2006

(65) Prior Publication Data

US 2008/0135789 A1    Jun. 12, 2008

(51) Int. Cl.
*G06K 9/00* (2006.01)
*A61B 6/00* (2006.01)

(52) U.S. Cl. .................. 382/128; 382/275; 378/16

(58) Field of Classification Search .............. 382/11, 382/128, 129, 130, 131, 132, 133, 134, 168, 382/181, 194, 199, 203, 232, 254, 260, 261–266, 382/274, 275, 276, 305, 312; 378/4, 5, 21, 378/50, 16; 250/252.1; 600/407
See application file for complete search history.

(56) References Cited

U.S. PATENT DOCUMENTS

| | | | | |
|---|---|---|---|---|
| 4,029,963 | A * | 6/1977 | Alvarez et al. | 378/5 |
| 4,571,491 | A * | 2/1986 | Vinegar et al. | 250/252.1 |
| 4,686,695 | A | 8/1987 | Macovski | |
| 6,973,158 | B2 * | 12/2005 | Besson | 378/16 |
| 6,975,894 | B2 * | 12/2005 | Wehrli et al. | 600/407 |
| 7,116,749 | B2 * | 10/2006 | Besson | 378/16 |
| 7,190,757 | B2 | 3/2007 | Ying et al. | |
| 7,197,172 | B1 * | 3/2007 | Naidu et al. | 382/131 |
| 2004/0184575 | A1 * | 9/2004 | Sikora | 378/50 |
| 2004/0223585 | A1 | 11/2004 | Heismann et al. | |
| 2008/0273666 | A1 | 11/2008 | Walter et al. | |

OTHER PUBLICATIONS

Alvarez et al., "Energy-Selective Reconstructions in X-Ray Computerized Tomography", Phys. Med. Biol., Voluume 21, No. 5, pp. 733-744, 1976.

Taguchi et al., "Image-Domain Material Decomposition Using Photon-Counting CT", Proc. of SPIE, vol. 6510, pp. 651008-1-651008-10, 2007.

(Continued)

*Primary Examiner*—Seyed Azarian
(74) *Attorney, Agent, or Firm*—Scott J. Asmus

(57) ABSTRACT

A diagnostic imaging system in an example includes a high frequency electromagnetic energy source, a detector, a data acquisition system (DAS), and a computer. The high frequency electromagnetic energy source emits a beam of high frequency electromagnetic energy toward an object to be imaged. The detector receives high frequency electromagnetic energy emitted by the high frequency electromagnetic energy source. The DAS is operably connected to the detector and programmed to employ a threshold to trigger a filter operation on a pixel, in a basis material decomposition (BMD) image of a plurality of BMD images, through comparison of an actual noise ratio between a pair of BMD images, of the plurality of BMD images, to a theoretical BMD noise ratio value. The computer is programmed to employ a correlation in noise distribution of the plurality of BMD images to reduce image noise in the plurality of BMD images.

20 Claims, 7 Drawing Sheets

OTHER PUBLICATIONS

Brody et al., "A Method for Selective Tissue and Bone Visualization Using Dual Energy Scanned Projection Radiography", Med. Phys., vol. 8, No. 3, pp. 353-357, May/Jun. 1981.

Walter et al., "Accuracy and Precision of Dual Energy CT Imaging for the Quantification of Tissue Fat Content", Proc. of SPIE, vol. 6142, pp. 61421G-1-61421G-12, 2006.

Heismann et al., "Density and Atomic Number Measurements With Spectral X-Ray Attenuation Method", Journal of Applied Physics, vol. 94, No. 3, pp. 2073-2079, Aug. 1, 2003.

Taibi et al., "Dual-Energy Imaging in Full-Field Digital Mammography: A Phantom Study", Phys. Med. Biol., vol. 48, pp. 1945-1956, 2003.

Marziani et al., "Dual-Energy Tissue Cancellation in Mammography With Quasi-Monochromatic X-Rays", Phys. Med. Biol., vol. 47, pp. 305-313, 2002.

Lehmann et al., "Generalized Image Combinations in Dual KVP Digital Radiography", Med. Phys., vol. 8, No. 5, pp. 659-667, Sep./Oct. 1981.

Kanai S. Shah, MS, A Novel Position Sensitive Detector for Nuclear Radiation, 2005.

Willi A. Kalender, Ernst Klotz, and Lena Kostaridou, An Algorithm for Noise Suppression in Dual Energy CT Material Density Images, IEEE Transactions on Medical Imaging, Vol. 7, No. 3, Sep. 1988.

* cited by examiner

MATERIAL DECOMPOSITION IMAGE NOISE REDUCTION

BACKGROUND OF THE INVENTION

The present invention relates generally to diagnostic imaging and, more particularly, to a method and apparatus of diagnostic imaging with material discrimination capabilities.

Exemplary diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

An exemplary CT imaging system comprises an energy discriminating (ED), multi energy (ME), and/or dual energy (DE) CT imaging system that may be referred to as an EDCT, MECT, and/or DE-CT imaging system. The EDCT, MECT, and/or DE-CT imaging system in an example is configured to be responsive to different x-ray spectra. For example, a conventional third generation CT system acquires projections sequentially at different x-ray tube potentials. Two scans in an example are acquired either back to back or interleaved in which the tube operates at 80 kVp and 160 kVp potentials. Special filters in an example are placed between the x-ray source and the detector such that different detector rows collect projections of different x-ray energy spectra. The filters are often placed between the x-ray source and the scanned object. The special filters that shape the x-ray spectrum in an example can be used for two scans that are acquired either back to back or interleaved. Energy sensitive detectors in an example are used such that each x-ray photon absorbed in the detector is recorded with its photon energy.

Exemplary ways to obtain the measurements comprise: (1) scan with two distinctive energy spectra, (2) detect photon energy according to energy deposition in the detector, and (3) photon counting with multiple energy bins. EDCT/MECT/DE-CT provides energy discrimination and material characterization. In the absence of object scatter, the system in an example derives the information about object attenuation versus energy based on the signal from two or more regions of photon energy in the spectrum, for example, the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two materials.

The conventional material basis decomposition or basis material decomposition (BMD) algorithm is based on the concept that in the energy region for medical CT, the x-ray attenuation of any given material can be represented by a proper density mix of two other materials, referred to as the basis materials. The BMD algorithm acquires two CT images. Each of the CT images represents the equivalent density of one of the basis materials. Since a material density is independent of x-ray photon energy, these images are approximately free of beam-hardening artifacts. An operator can choose the basis material to target a certain material of interest, for example, to enhance the image contrast.

Energy discrimination (ED) basis material decomposition (BMD) images are noisier than the conventional CT image. Conventional CT images represent the x-ray attenuation of an object under investigation. Without any energy information from the detection system, the conventional CT image cannot provide material characterization information. Two different materials with different densities may have similar CT numbers. In order to overcome this fundamental limitation and decode the BMD information, an exemplary EDCT system needs to separately detect at least two regions of photon energy spectrum: the low-energy and the high-energy portions of the incident x-ray spectrum. In another example, the EDCT system can detect all photons at different energies but with at least two different energy outputs (e.g., bins) that weight the photons differently as a function of energy. As a result, the total x-ray flux is divided into at least two subgroups. The quantum noise from each subgroup is larger than the quantum noise for the entire spectrum. Therefore, the material decomposition images are noisier than the conventional CT image at the same conditions. A typical way of decreasing image noise is using a linear filter that replaces each image pixel value with a weighted sum of pixels in a neighborhood of that pixel. Such a linear filter can be implemented in image space or Fourier space. In either case, a characteristic feature of a linear filter is that the noise decrease is accompanied by a spatial resolution decrease. Other filtering methods such a median filter or adaptive filter are nonlinear and can preserve sharp edges while reducing noise in regions of low gradient. Whereas the linear filter minimizes the mean-square difference, the median filter minimizes the absolute difference. A FIR-median filter is one that implements a median filter with increased and/or more optimum processing speed by reusing previous calculated results as moving from pixel to pixel. As will be understood by those skilled in the art, the median filter is implemented by replacing each pixel value by one of the values in the local neighborhood of pixels that minimizes the absolute difference summed over all the pixels in this neighborhood. Because such a calculation involves pairwise differences between pixel values, these pairwise differences can be precalculated and the sum made by combining these precomputed values for the neighborhood of the examined pixel. When filtering an image, one starts at some examined pixel location and replaces its value with the median value over the neighboring pixels. Then the next examined point in the data is processed by the filter. This requires a different sum, but this sum is closely related to the sum of the first examined pixel. The FIR-median filter makes use of this fact and only updates the sum as the filter method moves from pixel to pixel.

Therefore, it would be desirable to design an apparatus and method that employs response information from multiple bins and combines multi-bin data from neighboring pixels to reduce the noise of material decomposition images. It would be further desirable to decrease the noise with substantially little and/or minimal impact on the spatial resolution.

BRIEF DESCRIPTION OF THE INVENTION

The invention in an implementation encompasses a diagnostic imaging system. The diagnostic imaging system comprises a high frequency electromagnetic energy source, a detector, a data acquisition system (DAS), and a computer. The high frequency electromagnetic energy source emits a beam of high frequency electromagnetic energy toward an object to be imaged. The detector receives high frequency electromagnetic energy emitted by the high frequency electromagnetic energy source. The DAS is operably connected to the detector. The computer is operably connected to the DAS and programmed to employ a threshold to trigger a filter operation on a pixel, in a basis material decomposition (BMD) image of a plurality of BMD images, through comparison of an actual noise ratio between a pair of BMD images, of the plurality of BMD images, to a theoretical BMD noise ratio value. The computer operably connected to the DAS is programmed to employ a correlation in noise distribution of the plurality of BMD images to reduce image noise in the plurality of BMD images. The computer operably connected to the DAS is programmed to realize an adaptive algorithm through employment of an exponential correction function of a difference between the actual noise ratio and the theoretical BMD noise ratio value. The computer operably connected to the DAS is programmed to employ the adaptive algorithm to reduce the image noise in the plurality of BMD images.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Exemplary diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Exemplary applications of x-ray sources comprise imaging, medical, security, and industrial inspection applications. The operating environment of an exemplary implementation comprises a 64-slice CT system. However, it will be appreciated by those skilled in the art that an exemplary implementation is applicable for use with single-slice or other multi-slice configurations. Moreover, an exemplary implementation is employable for the detection and conversion of x-rays. However, one skilled in the art will further appreciate that an exemplary implementation is employable for the detection and conversion of other high frequency electromagnetic energy, high frequency polychromatic electromagnetic energy, and/or radiographic energy. An exemplary implementation is employable with a "third generation" CT scanner and/or other CT systems.

Figure 1:
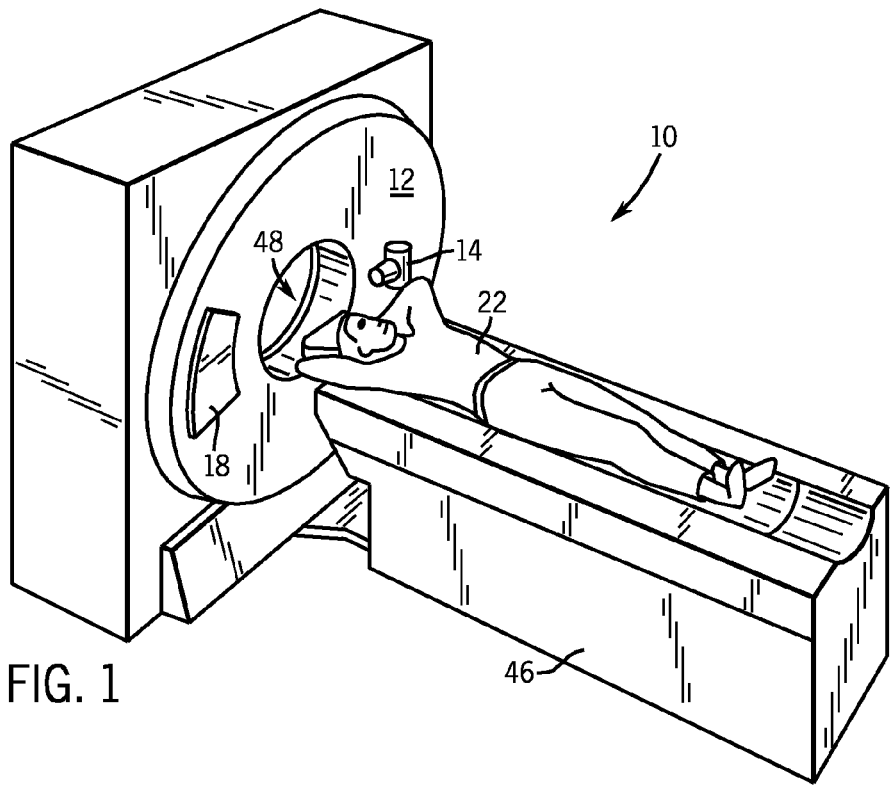
FIG. 1 is a pictorial view of a diagnostic and/or CT imaging system.
Figure 2:
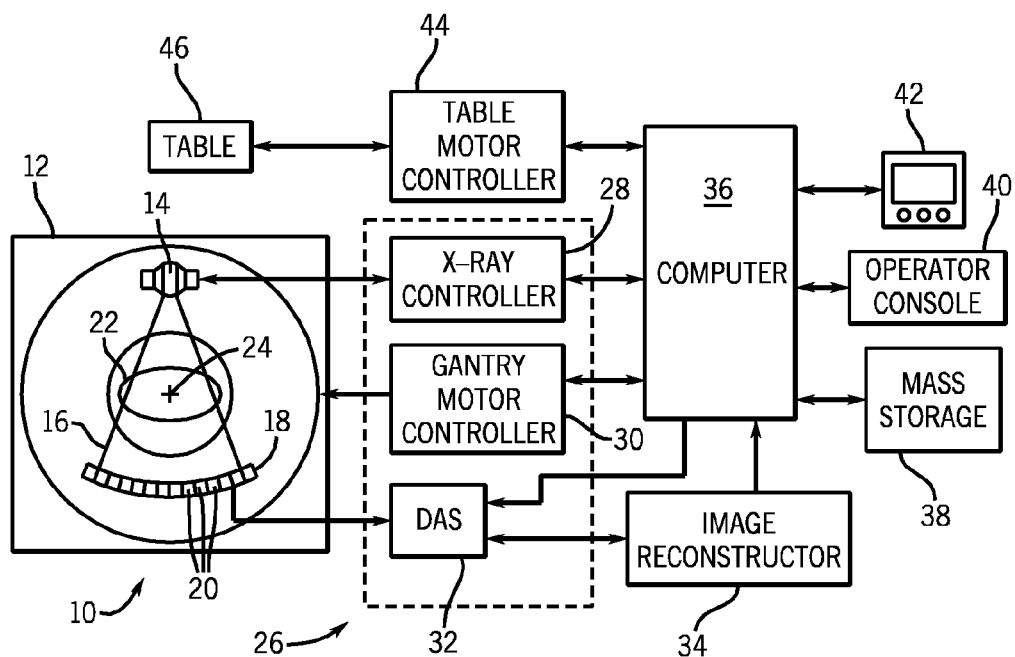
FIG. 2 is a block schematic diagram of the system illustrated in FIG. 1.

Referring to FIGS. 1 and 2, a diagnostic and/or CT imaging system 10 is shown as including a gantry 12 representative of a "third generation" CT scanner. The CT system 10 in an example comprises an energy discriminating (ED), multi energy (ME), and/or dual energy (DE) CT imaging system that may be referred to as an EDCT, MECT, and/or DE-CT imaging system. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. Exemplary detectors 20 comprise energy discriminating (ED) detectors, for example, photon counting x-ray detectors. The ED detector as the detector 20 in an example obtains ED readout from the beam of x-rays 16. During a scan to acquire x-ray projection data, gantry 12 and the components mounted thereon rotate about a center of rotation 24, as will be appreciated by those skilled in the art.

Rotation of gantry 12 and the operation of x-ray source 14 are governed by a control mechanism 26 of CT system 10. Control mechanism 26 includes an x-ray controller 28 that provides power and timing signals to the x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

EDCT/MECT/DE-CT provides energy discrimination and material characterization. For example, in the absence of object scatter, the system derives the behavior at any other energy based on the signal from two regions of photon energy in the spectrum: the low-energy and the high-energy portions of the incident x-ray spectrum. One or more exemplary techniques may serve to obtain spectral and/or energy information. Dual Kvps in an example may identify low energy from 80 to 100 kVp and high energy from 100 to 140 kVp. An exemplary photon counting energy discriminating detector may identify a threshold between the low and high energy at approximately 60-80 keV for a spectral between 100 to 140 kVp. An exemplary dual layer detector may obtain low energy information from a top layer and high energy information from a bottom layer. An exemplary energy integration detector with source filtration may obtain low energy information from an instance with less filtration and the high energy information from an instance with more filtration.

In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two materials.

An illustrative discussion is now presented in connection with an exemplary implementation of a decomposition algorithm, procedure, program, mechanism, application, code, and/or logic. An image or slice is computed which may incorporate, in certain modes, less or more than 360 degrees of projection data, to formulate an image. The image may be collimated to desired dimensions, using tungsten shutters in front of the x-ray source 14 and different detector apertures. A collimator typically defines the size and shape of the beam of x-rays 16 that emerges from the x-ray source 14. A bowtie filter may be included in the system 10 to further control the dose to the patient 22. An exemplary bowtie filter pre-attenuates the beam of x-rays 16 to accommodate the body part being imaged, such as head or torso, such that, in general, less attenuation is provided for x-rays passing through or near an isocenter of the patient 22. The bowtie filter in an example shapes the x-ray intensity during imaging in accordance with the region of interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In exemplary EDCT/MECT/DE-CT, two or more sets of projection data are obtained for the imaged object at different tube voltages or different x-ray spectra or, alternatively, at a single tube voltage or spectrum with an energy resolving detector of the detector array 18. The acquired sets of projection data may be used for material basis decomposition or basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes, and shapes of particular anatomies or organs, and other features that would be discernable in the image based upon the skill and knowledge of the individual practitioner.

Energy discrimination (ED) basis material decomposition (BMD) images display fundamentally different information compared to conventional CT images. In particular, the material composition of each image pixel is represented as a linear combination of densities of two basis materials. This representation of the composition of an imaging pixel can be pictured as a point in a 2-D plot where the x and y axes represent the densities of the basis materials. Due to the measurement noise of a CT system, a group of image pixels with a common material composition in an example lies within this 2-D plot as a group of points, for example, a point cloud, centered around, about, and/or on the actual composition point. The projection of the points in the 2-D plot to the x and y axes generates the basis material densities which comprise the gray-scale measures for the BMD images. There is a spread of the point cloud due to measurement noise. The point cloud spread is not isotropic but will be elongated in the azimuthally direction due to noise correlation created in the material decomposition algorithm. The spread of the point cloud, in particular in the azimuthal direction, causes the BMD images to be noisier than the traditional Hounsfield images of CT. Although they are noisier than the normal CT images, by visualizing and quantifying the information for some particular tissue or contrast materials, or removing some anatomic structure noise, the BMD images still can improve the conspicuity in many clinical applications. An exemplary implementation addresses the noisy nature of the BMD images.

In the basis material decomposition, the two basis material density $\rho_{m1}$ and $\rho_{m2}$ may be expressed as a polynomial function of the measured projection value at low and high energy $P_L$ and $P_H$, as in exemplary equations (1):

$$\rho_{m1} = a1 \cdot P_L + a2 \cdot P_L^2 + a3 \cdot P_L^3 + \ldots + b1 \cdot P_H + b2 \cdot P_H^2 + b3 \cdot P_H^3 + \ldots,$$

$$\rho_{m2} = c1 \cdot P_L + c2 \cdot P_L^2 + c3 \cdot P_L^3 + \ldots + d1 \cdot P_H + d2 \cdot P_H^2 + d3 \cdot P_H^3 + + \ldots,$$

where a, b, c, and d are polynomial coefficients, which depend on the low and high x-ray spectrum and the two basis material selection. These equations are dominated by the linear terms a1, b1, c1, and d1. In any particular measurement, if the measured projection value $P_L$ and $P_H$ change from their mean value by an error $\Delta pL$ and $\Delta pH$, then this error would also cause errors for the two basis material density by exemplary equations (2):

$$\Delta_{m1} = a1 \cdot \Delta_{PL} + b1 \cdot \Delta_{PH}$$

$$\Delta_{m2} = c1 \cdot \Delta_{PL} + d1 \cdot \Delta_{PH}$$

Therefore, there is a noise correlation in BMD images because each is a different linear combination of the same measured projection values $P_L$ and $P_H$. An exploration of the noise correlation serves to reduce noise in the images. Energy discrimination (ED) basis material decomposition (BMD) images are noisier than the conventional CT image. But the noise distributions of pixels values in the two BMD images are not independent with respect to each other. There is a strong correlation between them. By utilizing this correlation, an exemplary implementation employs an adaptive filtering algorithm, procedure, program, mechanism, application, code, and/or logic that serves to reduce the image noises in the two BMD images to improve the material separation capability. At the same time, the adaptive approach has only a small impact on the image spatial resolution.

An exemplary algorithm, procedure, program, mechanism, application, code, and/or logic exploits a correlation between noise in the two BMD images to reduce the image noises. An exemplary implementation applies in the image domain. An exemplary implementation applies in the projection domain. An exemplary implementation applies in the image domain and the projection domain. In the image domain in an example an implementation comprises a relative reduction in computational requirement and/or a relative increase in accuracy of noise estimation, as will be appreciated by those skilled in the art.

The computer 36 operably connected to the DAS 32 is programmed to employ the correlation in an image domain to reduce the image noise in the plurality of BMD images. The computer 36 operably connected to the DAS 32 is programmed to employ the correlation in a projection domain to reduce the image noise in the plurality of BMD images. The computer 36 operably connected to the DAS 32 is programmed to employ the correlation in an image domain and a projection domain to reduce the image noise in the plurality of BMD images.

An exemplary test of an exemplary implementation of the algorithm based on simulated data has demonstrated an ability of the algorithm to reduce the image noise in the BMD images while maintaining the system spatial resolution. By utilizing the correlation between the noises in the two BMD images, the image noise in an example may be reduced to improve the material separation capability. The computer 36 operably connected to the DAS 32 is programmed to employ the adaptive algorithm to improve material separation in the plurality of BMD images.

Figure 6:
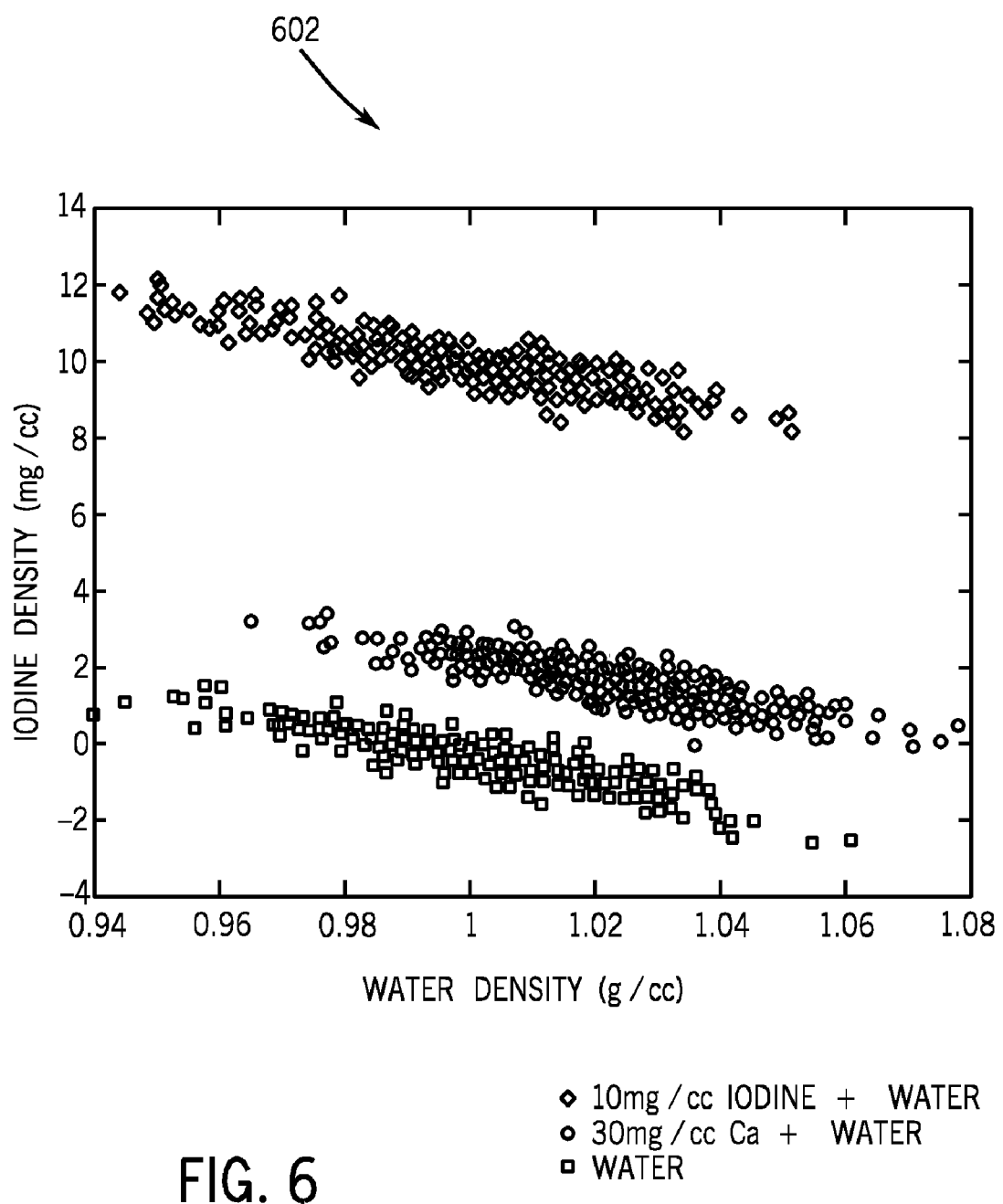
FIG. 6 is an exemplary plot of three material distribution for an original image.
Figure 7:
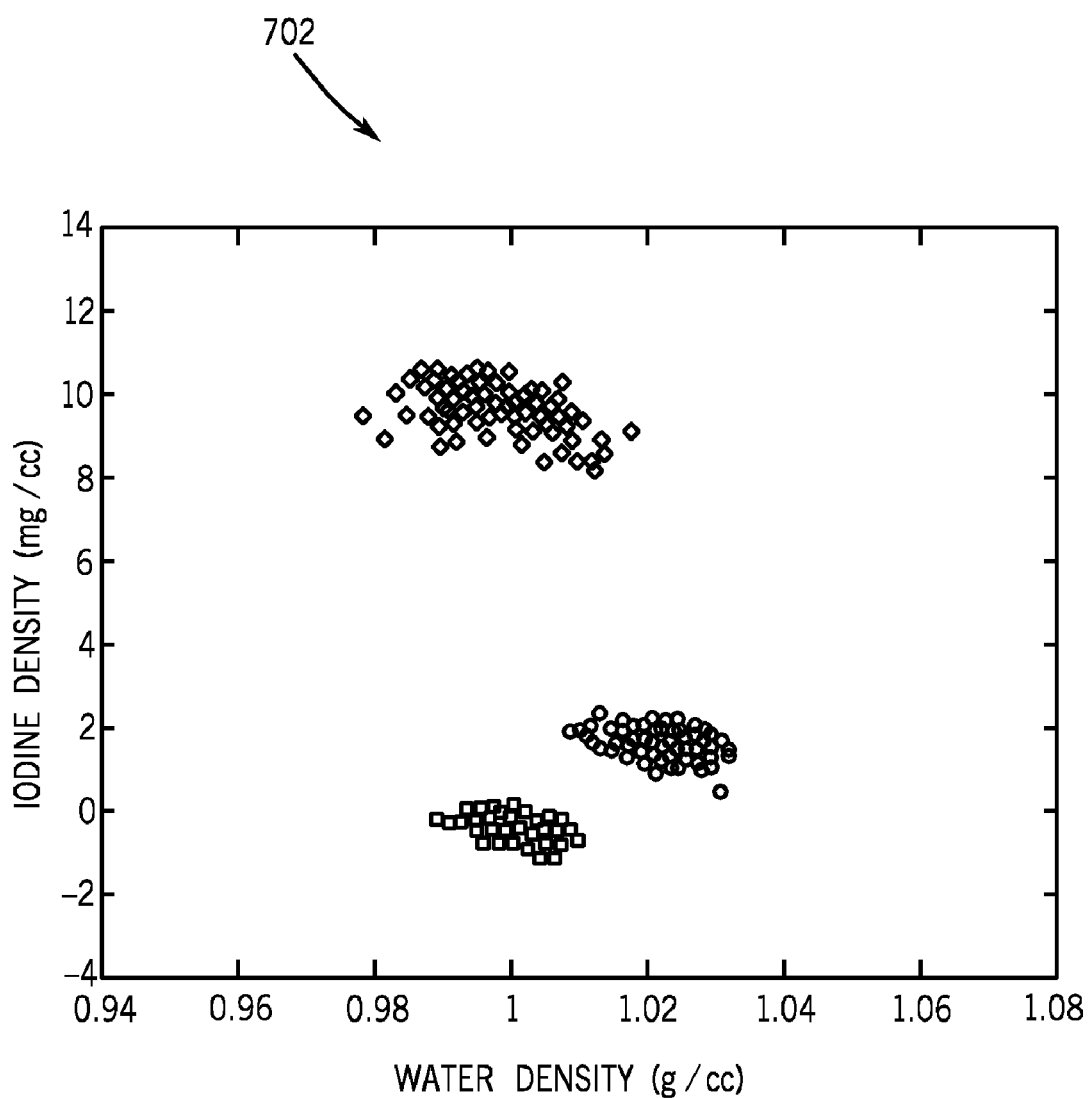
FIG. 7 is an exemplary plot of three material distribution for the image of FIG. 6 corrected through employment of the logic flow of FIG. 3.

FIG. 6 is an exemplary plot 602 of three material distribution for an original image. FIG. 7 is an exemplary plot 702 of three material distribution for the image corrected through employment of logic flow 302. The three material distribution in an example comprises 10 mg/cc Iodine and water; 30 mg/cc Calcium and water; and water. Due to the noise in an example the distribution of the three materials in the exemplary plot 602 is spread around the true location of the object 22 in the 2D basis material decomposition space. To separate these three materials, the three distribution regions in an example cannot overlap each other. The smaller and/or tighter the spread in an example the better the material separation that can be achieved. For the same simulated data in an example the material distribution spread in the exemplary plot 702 is relatively and/or substantially smaller and/or tighter, for example, to increase, enhance, and/or improve the material separation capability.

At the same time, an exemplary implementation of this adaptive approach has small impact on the image spatial resolution. An exemplary implementation examines a particular pixel and its adjacent and/or neighboring pixels to determine if the difference in pixel value of the examined pixel from some neighborhood average is likely to be caused by the measurement noise or more likely to be the result of the real structure of the projected field. If due to the measurement noise, then the value of the examined pixel is replaced by the average value. In this way the noise is reduced to improve the image. If the noise is not quantum based so the noise is due to change in material types such as at an edge of the image, then the noise is not subtracted. In the two BMD images, the image value for each pixel represents the basis material density in that pixel. Therefore, even without quantum noise, the image value will change near the structures in the object.

Referring again to FIGS. 1 and 3, the computer 36 operably connected to the DAS 32 is programmed to make the determination that the image noise in the particular pixel in the plurality of BMD images is not quantum-based upon a change in material types from the particular pixel to one or more adjacent pixels, of the plurality of pixels, in the plurality of BMD images. The computer 36 operably connected to the DAS 32 is programmed to make the determination that the image noise in the particular pixel in the plurality of BMD images is not quantum-based upon a location of the particular pixel at an edge of the plurality of BMD images. The average used can be the mean, median or mode. The implementation can adapt a FIR structure to reduce the computation time by leveraging calculations on previously examined pixels to speed the computations on the current pixel. The computer 36 operably connected to the DAS 32 is programmed to employ the adaptive algorithm with a substantially minor impact on image spatial resolution in the plurality of BMD images. The plurality of BMD images comprises a plurality of pixels. The computer 36 operably connected to the DAS 32 is programmed to make a determination whether or not image noise in a particular pixel in the plurality of BMD images is quantum-based. The computer 36 operably connected to the DAS 32 is programmed to upon the determination that the image noise in a particular pixel in the plurality of BMD images is not quantum-based, maintain the image noise in the particular pixel to maintain spatial resolution of the plurality of BMD images. The computer 36 operably connected to the DAS 32 is programmed to employ an adaptive algorithm, procedure, program, mechanism, application, code, and/or logic to reduce the image noise in the material decomposition images. The computer 36 operably connected to the DAS 32 is programmed to employ the adaptive algorithm, procedure, program, mechanism, application, code, and/or logic with a relatively small and/or substantially minimal impact on image spatial resolution in the material decomposition images.

Figure 3:
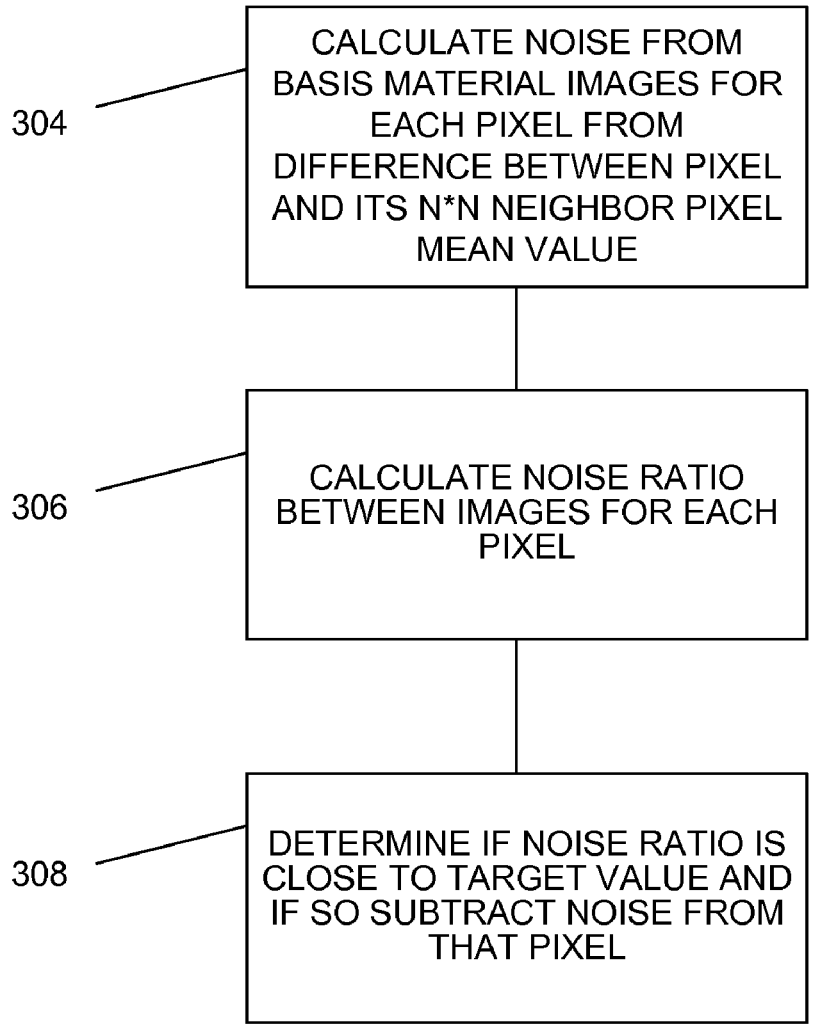
FIG. 3 is a representation of an exemplary logic flow for noise reduction in an implementation of the system of FIG. 1.

An illustrative description of an exemplary operation of an implementation of the system 10 is presented, for explanatory purposes. Turning to FIG. 3, in an exemplary algorithm, procedure, program, mechanism, application, code, and/or logic flow 302, STEP 304 in an example calculates noise from basis material images for each pixel from the difference between a pixel and its n×n neighbor pixel mean value. The image noise for both BMD images in an example is calculated. The noise from both basis material images is calculated for each pixel by calculating the difference between a pixel and its n×n neighbor pixel mean value, as in exemplary equation (3):

$$\Delta g_1 = g_1 - g_{1,n}^-, \Delta g_2 = g_2 - g_{2,n}^-$$

where g1 and g2 are the BMD material density for basis material 1 and material 2, $g_{1,n}^-$ $g_{2,n}^-$ are the mean value around n×n pixels, $\Delta g_1$ and $\Delta g2$ are the difference between a pixel and its n×n neighbor pixel mean value. These differences are used to represent the noise for each pixel. STEP 306 in an example calculates the noise ratio R between the images for each pixel. R=$\Delta g1/\Delta g2$. STEP 308 in an example determines if the noise ratio is close to a target and/or theoretical value and if so subtracts the noise from that pixel. The noise ratio in an example is determined to be close to the theoretical value and if so subtracts the noise from that pixel in both images. The noise ratio is compared with the theoretical value given by the material decomposition polynomial coefficient ratio. An exemplary material decomposition polynomial coefficient ratio is given by exemplary equations (1) and (2). If the actual noise ratio is close to the theoretical value, it is more likely that this noise is caused by the quantum noise. Thus the noise value is subtracted from both images. Otherwise, if the actual ratio is different from the theoretical value, STEP 308 determines that it is more likely the so calculated difference in STEP 304 is caused by the phantom (i.e. object or patient) structural material changes, not by the quantum noise, thus these pixels keep their original pixel value to maintain the spatial resolution. An exemplary implementation of this adaptive filtering is realized by an exponential correction function of the difference between the actual noise ratio and the theoretical value, as in exemplary equations (4):

$$g_{1c} = g_1 - \exp(-C|(R-tr)|)\Delta g_1$$

$$g_{2c} = g_2 - \exp(-C|(R-tr)|)\Delta g_2$$

where tr is the target/theoretical noise ratio between two BMD images, C is a control parameter to adjust the trade off between the noise and spatial resolution.

Figure 4:
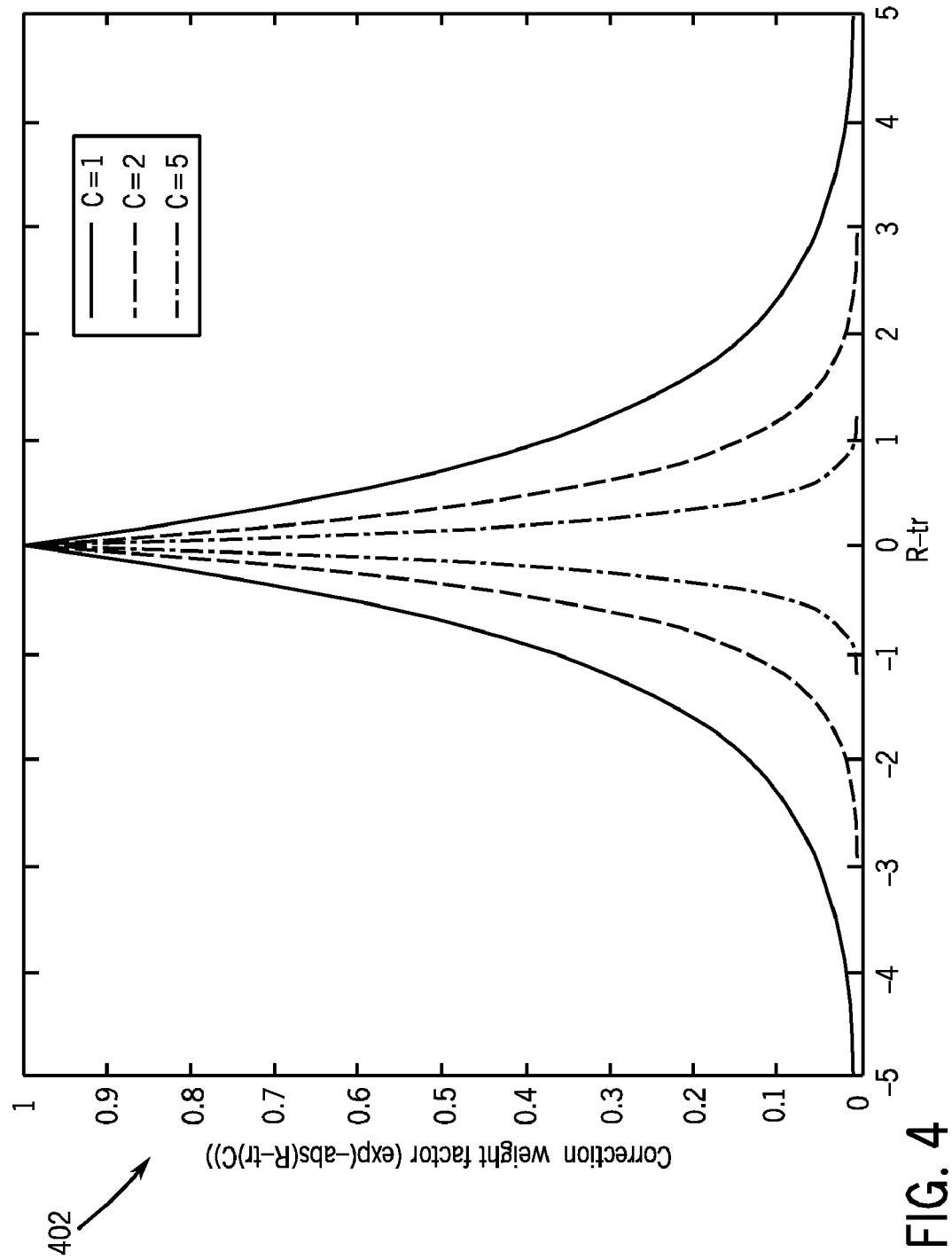
FIG. 4 is an exemplary plot of adjustment of a control parameter to change aggressiveness of an exponential correction function of a difference between an actual noise ratio and a target and/or theoretical value.

FIG. 4 is an exemplary plot 402 of adjustment of a control parameter to change aggressiveness of an exponential correction function of a difference between an actual noise ratio and a target and/or theoretical value. A control parameter C can be adjusted to change the aggressiveness of this correction. The exponential correction function in an example comprises a value of one when the measured noise ratio R is equal to the target and/or theoretical value tr. When the difference between R and tr is larger, the exponential correction function in an example becomes zero. The logic flow 302 serves to reduce the true noise due to the quantum fluctuations. The noise estimation is based on the difference between one pixel and its n×n neighboring pixels. For a uniform phantom, the bigger the number of the neighboring pixel n, the more accurate the noise estimation. For a real phantom with non-uniform structures, more pixels included in the noise estimation could induce bigger error around the edges. Therefore, in an exemplary implementation, the image pixel size n for the local mean value calculation can also be adjusted for trade off between the image noise and spatial resolution for any particular application.

Unlike the traditional local average filter, the logic flow 302 in an example behaves like a local average filter only when the noise ratio between the two material decomposition images is close to its theoretical value. An exemplary implementation adaptively reduces the noise in the material decompositions images while minimizing the impact on the system spatial resolution.

An exemplary implementation differs from a previous technique that calculates the difference of each pixel value from its local mean $\Delta g_1 = g_1 - g_{1,n}$, $\Delta g_2 = g_2 - g_{2,n}$, and that lacks an adaptive strategy making use of the ratio R $\Delta g1/\Delta g2$. The previous technique seeks to minimize the error in the monoenergetic image values derived from the filtered BMD images. The result is to apply the filter when the differences $\Delta g1$ and $\Delta g2$ are of opposite sign. That approach employs an ad hoc parameter adapt the filter to the presence of edges or structure in the images. In contrast, an exemplary implementation uses the ratio R and applies a theoretical target value tr against which the ratio is compared and the filter is most active when the ratio R is close to the target value. This target value may be calculated from the known physics of the system.

An exemplary threshold may be applied to the calculated image noise in both BMD images. If the image noises from both BMD images are smaller or less than the threshold, an exemplary implementation omits and/or withholds application of the adaptive filter, for example, to reduce the overall computation time. The plurality of BMD images comprises a first BMD image from a first BMD material and a second BMD image from a second BMD material, wherein the computer 36 operably connected to the DAS 32 is programmed to realize the adaptive algorithm through: calculation of the actual noise ratio at each pixel between the first BMD image and the second BMD image; and employment of the exponential correction function of the difference between the actual noise ratio and the theoretical BMD noise ratio value. The computer 36 operably connected to the DAS 32 is programmed to calculate a filtered image pixel value by application of the exponential function. The computer 36 operably connected to the DAS 32 is programmed to correct the filtered image pixel value to a local mean value when the actual noise ratio approximates and/or is substantially equal to the theoretical BMD noise ratio value.

The plurality of BMD images comprises a plurality of pixels. The computer 36 operably connected to the DAS 32 is programmed to subtract a particular image noise from a particular pixel, of the plurality of pixels, in the first BMD image and the second BMD image upon a determination that the actual noise ratio at the particular pixel between the first BMD image and the second BMD image approximates and/or is substantially equal to the theoretical BMD noise ratio value. The computer 36 operably connected to the DAS 32 is programmed to obtain the theoretical BMD noise ratio value from a BMD polynomial coefficient ratio for the actual noise ratio. The computer 36 operably connected to the DAS 32 is programmed to apply the theoretical BMD noise ratio value and the actual noise ratio in the exponential correction function to adjust an amount of filtering on the pixel in the first BMD image and the second BMD image. The computer 36 operably connected to the DAS 32 is programmed to select the theoretical ratio value to comprise a precalculated ratio that serves to characterize the diagnostic imaging system 10.

In an exemplary implementation, material decomposition coefficients such as in exemplary equations (1) and (2) may depend on the x-ray spectra, detector spectral response, and basis materials. An exemplary theoretical and/or target noise ratio R may also depend on system parameters such as the same and/or substantially the same system parameters, for example, the x-ray spectra, detector spectral response, and basis materials. An exemplary implementation may pre-calculate the target noise ratio R as a function of x-ray spectra, detector response, and basis materials and save the results in a lookup table. An exemplary image processing approach may select, choose, identify, and/or pick the target noise ratio R from the lookup table, for example, according to, in conformance with, under direction from, assisted by, and/or with guidance of the scan parameters.

The computer 36 is operably connected to the DAS 32 and programmed to retrieve a theoretical basis material decomposition (BMD) noise ratio value from a lookup table that is derived from a calibration procedure. The computer 36 operably connected to the DAS 32 is programmed to employ a threshold to trigger a filter operation on a pixel, in a BMD image of a plurality of BMD images, through comparison of an actual noise ratio between a pair of BMD images, of the plurality of BMD images, to the theoretical BMD noise ratio value. The computer 36 operably connected to the DAS 32 is programmed to employ a correlation in noise distribution of the plurality of BMD images to reduce image noise in the plurality of BMD images. The computer 36 operably connected to the DAS 32 is programmed to realize an adaptive algorithm through employment of an exponential correction function of a difference between the actual noise ratio and the theoretical BMD noise ratio value. The computer 36 operably connected to the DAS 32 is programmed to employ the adaptive algorithm to reduce the image noise in the plurality of BMD images.

An exemplary modulation transfer function may be unchanged in regions that have edges and contrast gradients and therefore preserve structure in the image. The image noises in an example are subtracted from only those pixels that have the noise ratio close, substantially near, and/or approximately equal to the target value. In the regions that have edges and contrast gradients, the noise ratio in an example is likely to not have the value close to and/or approximate the target value and in an exemplary implementation these pixels will keep their original values and preserve their intrinsic spatial resolution.

The computer 36 operably connected to the DAS 32 in an example is programmed to calculate the theoretical ratio value from a spectrum of the high frequency electromagnetic energy emitted by the high frequency electromagnetic energy source 14 and a response function of the detector 20 versus energy. In a further example, the theoretical ratio value is calculated from a spectrum of the high frequency electromagnetic energy emitted by the high frequency electromagnetic energy source 14 and a response function of the detector 20 versus energy. Exemplary calculation may occur on a computer 36 connected within the system 10 and/or an instance of the computer 36 separate, isolated, decoupled, and/or disconnected from one or more additional components of the system 10. The theoretical noise ratio in an example may be calculated by the computer 36 in a CT system 10 in real time, or may be precalculated by another computer. For example, a computer calculation may employ an additional instance of the computer 36 different from an instance of the computer 36 that later performs diagnostic imaging based on the computer simulation, as will be appreciated by those skilled in the art.

Figure 5:
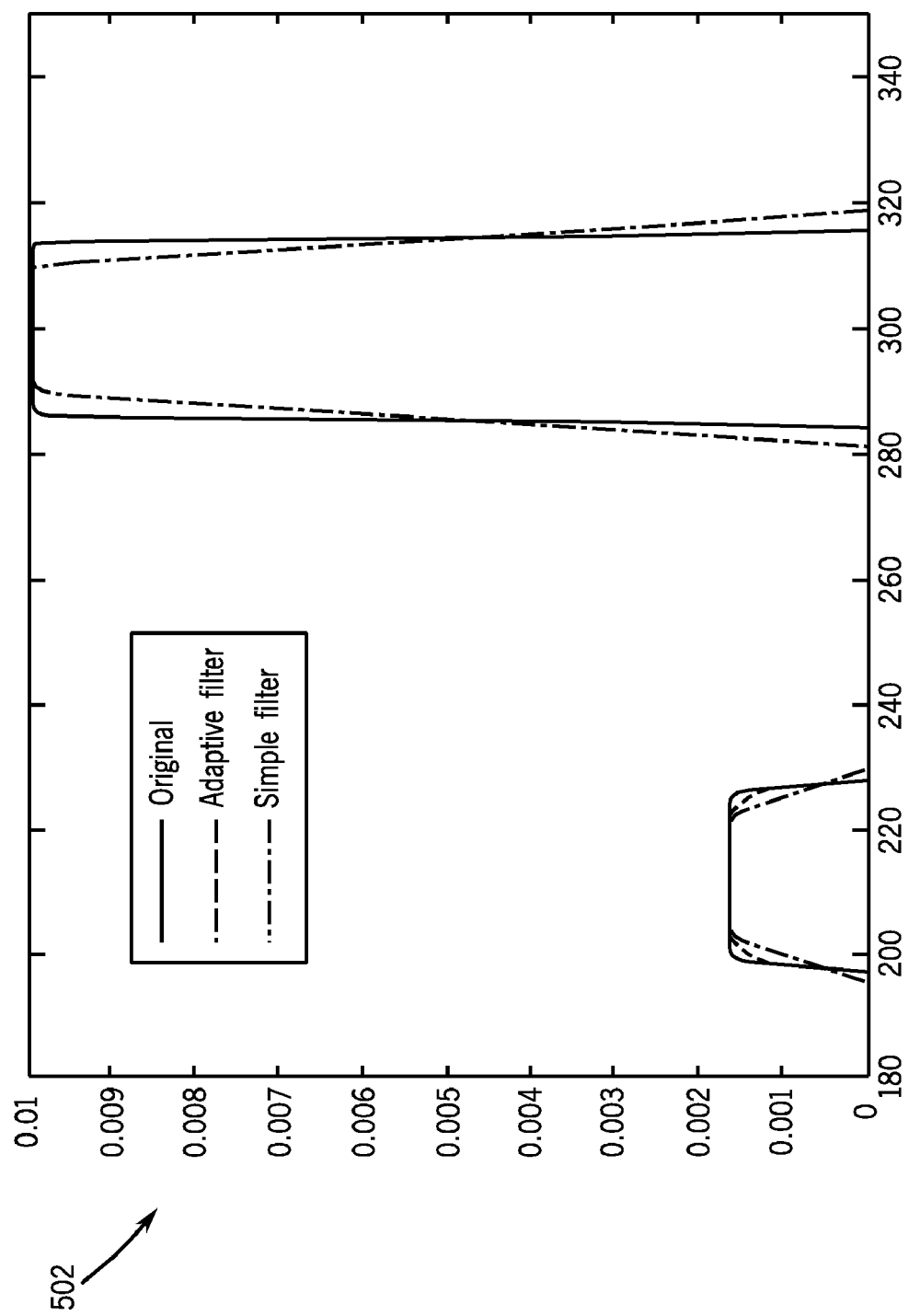
FIG. 5 is an exemplary plot of a line profile along a center row on a simulated phantom for an original image, an image from an adaptive filter that employs the logic flow of FIG. 3, and an image from a simple local average filter.

FIG. 5 is an exemplary plot 502 of the line profile along the center row on the simulated phantom for the original image, image with the new adaptive filter, and image with a simple local average filter. An exemplary line profile comprises the image intensity along a line. In an exemplary simulated image, the image size is 512×512. An exemplary center row comprises the $256^{th}$ row. Therefore, the line profile along the center row in an example comprises the image intensity along the $256^{th}$ row. An exemplary simulated phantom comprises a 30 cm diameter water circle. Within this water circle, there is a 1 cm diameter circle with 30 mg/cc Calcium on the left, and a 1 cm diameter circle with 10 mg/cc Iodine on the right. These 1 cm diameter circles in an example serve to represent blood vessels with different materials in them. Therefore, in FIG. 5 of the line profile, the left group is 30 mg/cc Calcium, and the right group is 10 mg/cc Iodine. Since the adaptive filter works so well that it does not distort the original iodine spatial resolution, the original line and adaptive filter line overlap with each other.

It is clear from these line profiles that the adaptive filter has very small impact on the system spatial resolution. Exemplary results have demonstrated the small impact of the logic flow 302 on the system spatial resolution. Exemplary results have demonstrated the ability of the logic flow 302 to reduce the noise from the material decomposition images at different quantum noise level.

In an exemplary implementation, a slope of the distribution is set by the theoretical value of the noise distribution. In an exemplary scanner, the value can be determined by theoretical calculation based on the x-ray tube spectrum and the detector spectral response. This value in an example can also be measured on the scanner with a uniform phantom.

As the noise in BMD images is correlated, the noise filter can be implemented in the 2-D space where the examined pixel value and its neighbors are implemented as vectors and the noise correlation captured in a correlation matrix. The asymmetry of the noise in the 2-D space is represented by the off-diagonal components of the correlation matrix and gives the slope in the logic flow 302. The noise correlation can be removed by a linear transformation that diagonalizes the correlation matrix. In this transformed space in an example the noise is isotropic and the filter logic flow 302 may proceed to replace the measured vector of the examined pixel with an average of the local neighborhood if the separation of the pixel from the mean is larger than that expected by the measurement noise.

An exemplary approach provides noise suppression in energy discrimination material decomposition ct images. An exemplary implementation provides diagnostic imaging with material discrimination capabilities using a system with selective response as a function of x-ray photon energy. An exemplary implementation makes an improved, enhanced, and/or best use of response information from multiple bins and combines multi-bin data from neighboring pixels to reduce the noise of material decomposition images. An exemplary approach, algorithm, procedure, program, mechanism, application, code, and/or logic serves to decrease the noise with reduced and/or minimal impact on the spatial resolution. An exemplary implementation uses one of the material decomposition images, or both, or even includes a conventional CT image, for example, depending on one or more particular applications.

An exemplary implementation comprises a high frequency electromagnetic energy source 14, a detector 18, 20, a data acquisition system (DAS) 32, and a computer 36. The high frequency electromagnetic energy source 14 emits a beam 16 of high frequency electromagnetic energy toward an object 22 to be imaged. The detector 18, 20 receives high frequency electromagnetic energy emitted by the high frequency electromagnetic energy source 14. The DAS 32 is operably connected to the detector 18, 20. The computer 36 is operably connected to the DAS 32 and programmed to employ a threshold to trigger a filter operation on a pixel, in a basis material decomposition (BMD) image of a plurality of BMD images, through comparison of an actual noise ratio between a pair of BMD images, of the plurality of BMD images, to a theoretical BMD noise ratio value. The computer 36 operably connected to the DAS 32 is programmed to employ a correlation in noise distribution of the plurality of BMD images to reduce image noise in the plurality of BMD images. The computer 36 operably connected to the DAS 32 is programmed to realize an adaptive algorithm through employment of an exponential correction function of a difference between the actual noise ratio and the theoretical BMD noise ratio value. The computer 36 operably connected to the DAS 32 is programmed to employ the adaptive algorithm to reduce the image noise in the plurality of BMD images.

The computer 36 operably connected to the DAS 32 is programmed to employ the adaptive algorithm to improve material separation in the plurality of BMD images. The computer 36 operably connected to the DAS 32 is programmed to select the theoretical ratio value to comprise a precalculated ratio that serves to characterize the diagnostic imaging system 10. The computer 36 operably connected to the DAS 32 is programmed to employ the adaptive algorithm with a substantially minor impact on image spatial resolution in the plurality of BMD images.

The computer 36 operably connected to the DAS 32 is programmed to employ the correlation in an image domain to reduce the image noise in the plurality of BMD images. The computer 36 operably connected to the DAS 32 is programmed to employ the correlation in a projection domain to reduce the image noise in the plurality of BMD images.

The plurality of BMD images comprises a plurality of pixels. The computer 36 operably connected to the DAS 32 is programmed to make a determination whether or not image noise in a particular pixel, of the plurality of pixels, in the plurality of BMD images is quantum-based. The computer 36 operably connected to the DAS 32 is programmed to upon the determination that the image noise in the particular pixel in the plurality of BMD images is quantum-based, subtract the image noise from the particular pixel to improve image quality of the plurality of BMD images. The computer 36 operably connected to the DAS 32 is programmed to make a determination whether or not image noise in a particular pixel, of the plurality of pixels, in the plurality of BMD images is quantum-based. The computer 36 operably connected to the DAS 32 is programmed to upon the determination that the image noise in a particular pixel in the plurality of BMD images is not quantum-based, maintain the image noise in the particular pixel to maintain spatial resolution of the plurality of BMD images.

The computer 36 operably connected to the DAS 32 is programmed to make a determination whether or not image noise in the particular pixel in the plurality of BMD images is quantum-based. The computer 36 operably connected to the DAS 32 is programmed to make the determination that the image noise in the particular pixel in the plurality of BMD images is not quantum-based upon a change in material types from the particular pixel to one or more adjacent pixels, of the plurality of pixels, in the plurality of BMD images. The computer 36 operably connected to the DAS 32 is programmed to make the determination that the image noise in the particular pixel in the plurality of BMD images is not quantum-based upon a location of the particular pixel at an edge of the plurality of BMD images. The computer 36 operably connected to the DAS 32 is programmed to calculate image noise in a BMD image of the plurality of BMD images through calculation of a difference between a pixel and an n×n neighbor pixel mean value for the pixel in the BMD image.

The plurality of BMD images comprises a first BMD image from a first BMD material and a second BMD image from a second BMD material, wherein the computer 36 operably connected to the DAS 32 is programmed to realize the adaptive algorithm through: calculation of the actual noise ratio at each pixel between the first BMD image and the second BMD image; and employment of the exponential correction function of the difference between the actual noise ratio and the theoretical BMD noise ratio value. The computer 36 operably connected to the DAS 32 is programmed to calculate a filtered image pixel value by application of the exponential function. The computer 36 operably connected to the DAS 32 is programmed to correct the filtered image pixel value to a local mean value when the actual noise ratio approximates and/or is substantially equal to the theoretical BMD noise ratio value. The plurality of BMD images comprises a plurality of pixels. The computer 36 operably connected to the DAS 32 is programmed to subtract a particular image noise from a particular pixel, of the plurality of pixels, in the first BMD image and the second BMD image upon a determination that the actual noise ratio at the particular pixel between the first BMD image and the second BMD image approximates and/or is substantially equal to the theoretical BMD noise ratio value.

The computer 36 operably connected to the DAS 32 is programmed to obtain the theoretical BMD noise ratio value from a BMD polynomial coefficient ratio for the actual noise ratio. The computer 36 operably connected to the DAS 32 is programmed to apply the theoretical BMD noise ratio value and the actual noise ratio in the exponential correction function to adjust an amount of filtering on the pixel in the first BMD image and the second BMD image. The computer 36 operably connected to the DAS 32 is programmed to interpret the correlation in noise distribution of the plurality of BMD images as a different linear combination of same measured projection values at low and high energies. The computer 36 operably connected to the DAS 32 is programmed to interpret the low and high energies as effective mean energies over an absorbed spectrum of the high frequency electromagnetic energy emitted by the high frequency electromagnetic energy source 14.

An exemplary implementation comprises a high frequency electromagnetic energy source 14, a detector 18, 20, a data acquisition system (DAS) 32, and a computer 36. The high frequency electromagnetic energy source 14 emits a beam 16 of high frequency electromagnetic energy toward an object 22 to be imaged. The detector 18, 20 receives high frequency electromagnetic energy emitted by the high frequency electromagnetic energy source 14. The DAS 32 is operably connected to the detector 18, 20. The computer 36 is operably connected to the DAS 32 and programmed to retrieve a theoretical basis material decomposition (BMD) noise ratio value from a lookup table that is derived from a calibration procedure. The computer 36 operably connected to the DAS 32 is programmed to employ a threshold to trigger a filter operation on a pixel, in a BMD image of a plurality of BMD images, through comparison of an actual noise ratio between a pair of BMD images, of the plurality of BMD images, to the theoretical BMD noise ratio value. The computer 36 operably connected to the DAS 32 is programmed to employ a correlation in noise distribution of the plurality of BMD images to reduce image noise in the plurality of BMD images. The computer 36 operably connected to the DAS 32 is programmed to realize an adaptive algorithm through employment of an exponential correction function of a difference between the actual noise ratio and the theoretical BMD noise ratio value. The computer 36 operably connected to the DAS 32 is programmed to employ the adaptive algorithm to reduce the image noise in the plurality of BMD images.

The computer 36 operably connected to the DAS 32 is programmed to calculate the theoretical ratio value from a spectrum of the high frequency electromagnetic energy emitted by the high frequency electromagnetic energy source 14 and a response function of the detector 18, 20 versus energy. The theoretical ratio value is calculated from a spectrum of the high frequency electromagnetic energy emitted by the high frequency electromagnetic energy source 14 and a response function of the detector 18, 20 versus energy.

An exemplary implementation comprises a high frequency electromagnetic energy source 14, a detector 18, 20, a data acquisition system (DAS) 32, and a computer 36. The high frequency electromagnetic energy source 14 emits a beam 16 of high frequency electromagnetic energy toward an object 22 to be imaged. The detector 18, 20 receives high frequency electromagnetic energy emitted by the high frequency electromagnetic energy source 14. The DAS 32 is operably connected to the detector 18, 20. The computer 36 is operably connected to the DAS 32 and programmed to combine response information from multiple energy bins for neighboring pixels to reduce image noise in material decomposition images. The computer 36 operably connected to the DAS 32 is programmed to employ a correlation in noise distribution of the material decomposition images to reduce the image noise. The computer 36 operably connected to the DAS 32 is programmed to employ an adaptive algorithm, procedure, program, mechanism, application, code, and/or logic to reduce the image noise in the material decomposition images. The computer 36 operably connected to the DAS 32 is programmed to employ the adaptive algorithm, procedure, program, mechanism, application, code, and/or logic with a relatively small and/or substantially minimal impact on image spatial resolution in the material decomposition images.

Figure 8:
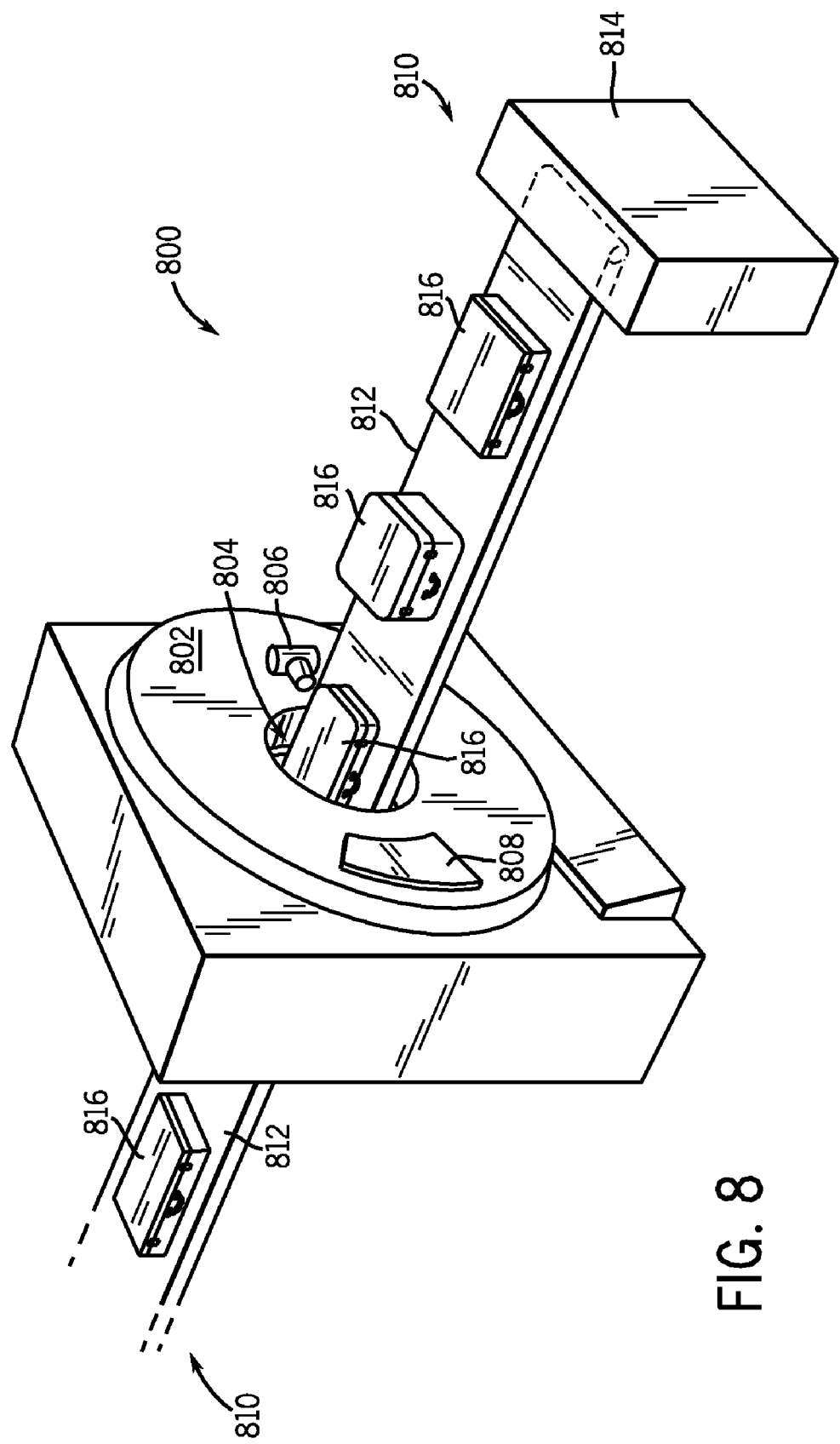
FIG. 8 is a pictorial view of a diagnostic and/or CT system for use with a non-invasive package inspection system.

Referring now to FIG. 8, package/baggage inspection system 100 includes a rotatable gantry 802 having an opening 804 therein through which packages or pieces of baggage may pass. The rotatable gantry 802 houses an x-ray and/or high frequency electromagnetic energy source 806 as well as a detector assembly 808 having scintillator arrays comprised of scintillator cells. A conveyor system 810 is also provided and includes a conveyor belt 812 supported by structure 814 to automatically and continuously pass packages or baggage pieces 816 through opening 804 to be scanned. Objects 816 are fed through opening 804 by conveyor belt 812, imaging data is then acquired, and the conveyor belt 812 removes the packages 816 from opening 804 in a controlled and continuous manner. As a result, postal inspectors, baggage handlers, and other security personnel may non-invasively inspect the contents of packages 816 for explosives, knives, guns, contraband, etc.

An implementation of the system 10 and/or 100 in an example comprises a plurality of components such as one or more of electronic components, hardware components, and/or computer software components. A number of such components can be combined or divided in an implementation of the system 10 and/or 100. An exemplary component of an implementation of the system 10 and/or 100 employs and/or comprises a set and/or series of computer instructions written in or implemented with any of a number of programming languages, as will be appreciated by those skilled in the art. An exemplary technical effect is one or more exemplary and/or desirable functions, approaches, and/or procedures. An implementation of the system 10 and/or 100 in an example comprises any (e.g., horizontal, oblique, or vertical) orientation, with the description and figures herein illustrating an exemplary orientation of an implementation of the system 10 and/or 100, for explanatory purposes.

An implementation of the system 10 and/or the system 100 encompasses an article. The article comprises one or more computer-readable signal-bearing media. The article comprises means in the one or more media for one or more exemplary and/or desirable functions, approaches, and/or procedures.

An implementation of the system 10 and/or the system 100 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 100 comprises the recordable data storage medium of the image reconstructor 34, and/or the mass storage device 38 of the computer 36. A computer-readable signal-bearing medium for an implementation of the system 10 and/or the system 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 100, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified The present invention has been described in terms of the preferred embodiment, and it is recognized that equivalents, alternatives, and modifications, aside from those expressly stated, are possible and within the scope of the appending claims.

What is claimed is:

1. A diagnostic imaging system, comprising:
    a high frequency electromagnetic energy source that emits a beam of high frequency electromagnetic energy toward an object to be imaged;
    a detector that receives high frequency electromagnetic energy emitted by the high frequency electromagnetic energy source;
    a data acquisition system (DAS) operably connected to the detector; and
    a computer operably connected to the DAS and programmed to:
        employ a threshold to trigger a filter operation on a pixel, in a basis material decomposition (BMD) image of a plurality of BMD images, through comparison of an actual noise ratio between a pair of BMD images, of the plurality of BMD images, to a theoretical BMD noise ratio value;
        employ a correlation in noise distribution of the plurality of BMD images to reduce image noise in the plurality of BMD images;
        realize an adaptive algorithm through employment of an exponential correction function of a difference between the actual noise ratio and the theoretical BMD noise ratio value; and
        employ the adaptive algorithm to reduce the image noise in the plurality of BMD images.

2. The diagnostic imaging system of claim 1, wherein the computer operably connected to the DAS is programmed to employ the adaptive algorithm to improve material separation in the plurality of BMD images.

3. The diagnostic imaging system of claim 1, wherein the computer operably connected to the DAS is programmed to:
    select the theoretical ratio value to comprise a precalculated ratio that serves to characterize the diagnostic imaging system.

4. The diagnostic imaging system of claim 1, wherein the computer operably connected to the DAS is programmed to:

employ the adaptive algorithm with a substantially minor impact on image spatial resolution in the plurality of BMD images.

5. The diagnostic imaging system of claim 1, wherein the computer operably connected to the DAS is programmed to employ the correlation in an image domain to reduce the image noise in the plurality of BMD images.

6. The diagnostic imaging system of claim 1, wherein the computer operably connected to the DAS is programmed to employ the correlation in a projection domain to reduce the image noise in the plurality of BMD images.

7. The diagnostic imaging system of claim 1, wherein the plurality of BMD images comprises a plurality of pixels, wherein the computer operably connected to the DAS is programmed to:
   make a determination whether or not image noise in a particular pixel, of the plurality of pixels, in the plurality of BMD images is quantum-based; and
   upon the determination that the image noise in the particular pixel in the plurality of BMD images is quantum-based, subtract the image noise from the particular pixel to improve image quality of the plurality of BMD images.

8. The diagnostic imaging system of claim 1, wherein the plurality of BMD images comprises a plurality of pixels, wherein the computer operably connected to the DAS is programmed to:
   make a determination whether or not image noise in a particular pixel, of the plurality of pixels, in the plurality of BMD images is quantum-based; and
   upon the determination that the image noise in a particular pixel in the plurality of BMD images is not quantum-based, maintain the image noise in the particular pixel to maintain spatial resolution of the plurality of BMD images.

9. The diagnostic imaging system of claim 8, wherein the computer operably connected to the DAS is programmed to:
   make a determination whether or not image noise in the particular pixel in the plurality of BMD images is quantum-based; and
   make the determination that the image noise in the particular pixel in the plurality of BMD images is not quantum-based upon a change in material types from the particular pixel to one or more adjacent pixels, of the plurality of pixels, in the plurality of BMD images.

10. The diagnostic imaging system of claim 8, wherein the computer operably connected to the DAS is programmed to:
    make a determination whether or not image noise in the particular pixel in the plurality of BMD images is quantum-based; and
    make the determination that the image noise in the particular pixel in the plurality of BMD images is not quantum-based upon a location of the particular pixel at an edge of the plurality of BMD images.

11. The diagnostic imaging system of claim 1, wherein the computer operably connected to the DAS is programmed to:
    calculate image noise in a BMD image of the plurality of BMD images through calculation of a difference between a pixel and an n×n neighbor pixel mean value for the pixel in the BMD image.

12. The diagnostic imaging system of claim 1, wherein the plurality of BMD images comprises a first BMD image from a first BMD material and a second BMD image from a second BMD material, wherein the computer operably connected to the DAS is programmed to:
    realize the adaptive algorithm through:
        calculation of the actual noise ratio at each pixel between the first BMD image and the second BMD image;
        employment of the exponential correction function of the difference between the actual noise ratio and the theoretical BMD noise ratio value;
    calculate a filtered image pixel value by application of the exponential function; and
    correct the filtered image pixel value to a local mean value when the actual noise ratio approximates and/or is substantially equal to the theoretical BMD noise ratio value.

13. The diagnostic imaging system of claim 12, wherein the plurality of BMD images comprises a plurality of pixels, wherein the computer operably connected to the DAS is programmed to:
    subtract a particular image noise from a particular pixel, of the plurality of pixels, in the first BMD image and the second BMD image upon a determination that the actual noise ratio at the particular pixel between the first BMD image and the second BMD image approximates and/or is substantially equal to the theoretical BMD noise ratio value.

14. The diagnostic imaging system of claim 13, wherein the computer operably connected to the DAS is programmed to obtain the theoretical BMD noise ratio value from a BMD polynomial coefficient ratio for the actual noise ratio.

15. The diagnostic imaging system of claim 14, wherein the computer operably connected to the DAS is programmed to apply the theoretical BMD noise ratio value and the actual noise ratio in the exponential correction function to adjust an amount of filtering on the pixel in the first BMD image and the second BMD image.

16. The diagnostic imaging system of claim 1, wherein the computer operably connected to the DAS is programmed to:
    interpret the correlation in noise distribution of the plurality of BMD images as a different linear combination of same measured projection values at low and high energies; and
    interpret the low and high energies as effective mean energies over an absorbed spectrum of the high frequency electromagnetic energy emitted by the high frequency electromagnetic energy source.

17. A diagnostic imaging system, comprising:
    a high frequency electromagnetic energy source that emits a beam of high frequency electromagnetic energy toward an object to be imaged;
    a detector that receives high frequency electromagnetic energy emitted by the high frequency electromagnetic energy source;
    a data acquisition system (DAS) operably connected to the detector; and
    a computer operably connected to the DAS and programmed to:
        retrieve a theoretical basis material decomposition (BMD) noise ratio value from a lookup table that is derived from a calibration procedure;
        employ a threshold to trigger a filter operation on a pixel, in a BMD image of a plurality of BMD images, through comparison of an actual noise ratio between a pair of BMD images, of the plurality of BMD images, to the theoretical BMD noise ratio value;
        employ a correlation in noise distribution of the plurality of BMD images to reduce image noise in the plurality of BMD images;
        realize an adaptive algorithm through employment of an exponential correction function of a difference between the actual noise ratio and the theoretical BMD noise ratio value; and employ the adaptive algorithm to reduce the image noise in the plurality of BMD images.

18. The diagnostic imaging system of claim 17, wherein the computer operably connected to the DAS is programmed to:
calculate the theoretical ratio value from a spectrum of the high frequency electromagnetic energy emitted by the high frequency electromagnetic energy source and a response function of the detector versus energy.

19. The diagnostic imaging system of claim 17, wherein the theoretical ratio value is calculated from a spectrum of the high frequency electromagnetic energy emitted by the high frequency electromagnetic energy source and a response function of the detector versus energy.

20. A diagnostic imaging system, comprising:
a high frequency electromagnetic energy source that emits a beam of high frequency electromagnetic energy toward an object to be imaged;
a detector that receives high frequency electromagnetic energy emitted by the high frequency electromagnetic energy source;
a data acquisition system (DAS) operably connected to the detector; and
a computer operably connected to the DAS and programmed to:
combine response information from multiple energy bins for neighboring pixels to reduce image noise in material decomposition images;
employ a correlation in noise distribution of the material decomposition images to reduce the image noise;
employ an adaptive algorithm, procedure, program, mechanism, application, code, and/or logic to reduce the image noise in the material decomposition images; and
employ the adaptive algorithm, procedure, program, mechanism, application, code, and/or logic with a relatively small and/or substantially minimal impact on image spatial resolution in the material decomposition images.

* * * * *